United States Patent [19]

Fennhoff et al.

[11] Patent Number: 5,376,715
[45] Date of Patent: Dec. 27, 1994

[54] HEAT STABILIZATION OR AROMATIC POLYCARBONATES

[75] Inventors: Gerhard Fennhoff, Willich; Jürgen Kirsch, Leverkusen; Karsten-Josef Idel, Krefeld; Klaus Kircher, Leverkusen, all of Germany; Charles Lundy, Pittsburgh, Pa.

[73] Assignees: Bayer Aktiengesellschaft, Leverkusen, Germany; Miles Inc., Pittsburgh, Pa.

[21] Appl. No.: 183,096

[22] Filed: Jan. 18, 1994

Related U.S. Application Data

[63] Continuation of Ser. No. 48,703, Apr. 16, 1993, abandoned.

[30] Foreign Application Priority Data

Apr. 23, 1992 [DE] Germany ............................. 4213321

[51] Int. Cl.$^5$ ................................................ C08K 5/24
[52] U.S. Cl. ..................................... 524/265; 556/453; 556/457; 556/464; 556/474; 556/482; 556/489
[58] Field of Search ............... 524/265; 556/453, 457, 556/464, 474, 482, 489

[56] References Cited

U.S. PATENT DOCUMENTS

| | | | |
|---|---|---|---|
| 4,197,384 | 4/1980 | Bialous, deceased et al. | 525/464 |
| 4,342,681 | 8/1982 | Idel et al. | 524/108 |
| 4,367,303 | 1/1983 | Eimers et al. | 524/107 |
| 4,375,525 | 3/1983 | Idel et al. | 524/108 |
| 4,397,973 | 8/1983 | Scott et al. | 524/114 |
| 4,456,717 | 6/1984 | Eimers et al. | 524/108 |
| 4,467,105 | 8/1984 | Kötzsch | 556/444 |
| 4,804,692 | 2/1989 | Lundy et al. | 523/137 |

FOREIGN PATENT DOCUMENTS

| | | |
|---|---|---|
| 376289 | 7/1990 | European Pat. Off. . |
| 4118705 | 1/1993 | Germany . |
| 4127079 | 1/1993 | Germany . |
| 1203869 | 9/1970 | United Kingdom . |
| 1595701 | 8/1981 | United Kingdom . |

OTHER PUBLICATIONS

The Journal of Organic Chemistry, vol. 58, 1958, pp. 58–64, M. M. Sprung.
Zhurnal Obshchei Khimii, vol. 28, No. 10, 1988, pp. 2274–2281, A. A. Krolevets et al.
Chemical Abstracts, vol. 108, 1988, Abstract No. 75464m, S. Hardin et al.
Chemical Abstracts, vol. 115, 1991, Abstract No. 30488a, H. Kim-Kang et al.

*Primary Examiner*—Melvyn I. Marquis
*Attorney, Agent, or Firm*—Joseph C. Gil; Aron Preis

[57] ABSTRACT

The invention relates to silicon compounds, to mixtures thereof in aromatic polycarbonates and aromatic polyester carbonates and to their use as heat stabilizers in aromatic polycarbonates and aromatic polyester carbonates.

1 Claim, No Drawings

HEAT STABILIZATION OR AROMATIC POLYCARBONATES

This application is a continuation of application Ser. No. 08/048,703 filed Apr. 16, 1993, now abandoned.

This invention relates to silicon compounds corresponding to formulae (I)

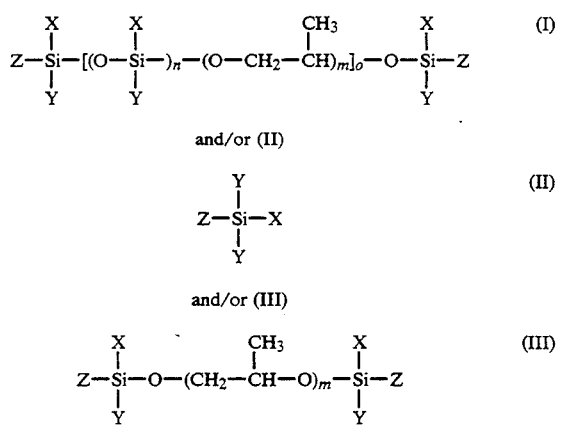

in which
X represents hydrogen [only for formula (I)], $C_1$-$C_{20}$- preferably $C_{1-10}$alkyl, -alkoxy, -alkylether, -alkoxyether, -aryl or $C_{3-10}$ alkoxyoxetane, Y represents hydrogen, $C_1$-$C_2$- preferably $C_{1-10}$ alkyl, -alkoxy, -alkylether, -alkoxyether, -aryl or $C_{3-10}$ alkoxyoxetane, Z represents phenyl, $C_{1-10}$ alkyl; the alkyl may be branched and/or unbranched, n is an integer of 1 to 100, preferably 1 to 50 and, more preferably, 1 to 20, m is an integer of 1 to 100, preferably 1 to 50 and, more preferably 1 to 20 and o is an integer of 1 to 100, preferably 1 to 50 and, more preferably 1 to 20.

The silicon compounds corresponding to formulae (I), (II) and (III) are synthesized by the standard methods described in the literature (see, for example, Houben-Weyl, Methoden der Organisthen Chemic, Vol. XIII/5, Organo-Silicium-Verbindungen (Organosilicon Compounds), Georg Thieme Verlag, Stuttgart/New York, 1980, pages 199 et seq.).

The present invention also relates to aromatic polycarbonates and/or aromatic polyester carbonates containing 0.01% by weight to 20% by weight, preferably 0.01% by weight to 10.0% by weight and especially 0.05% by weight to 5.0% by weight, based on the quantity of polycarbonate and/or polyester carbonate used, of silicon compounds corresponding to formulae (1) and/or (II) and/or (III) above.

By virtue of their physical properties, the thermoplastic polycarbonates and/or polyester carbonates are suitable for optical applications, particularly at relatively high temperatures. For applications in this field, it is important that the corresponding articles and moldings of the thermoplastic polycarbonates and/or polyester carbonates have excellent transmission and color.

However, processing by extrusion and injection molding and hot air ageing cause permanent damage to the polycarbonates and polyester carbonates in the form of yellowing. Such damage, which is attributable to the effect of high temperatures (i.e. extrusion, injection molding or hot air ageing) is largely suppressed by using silicon/propylene glycol compounds in accordance with the present invention.

There are various methods for protecting thermoplastic polycarbonates and polyester carbonates against the effects of high temperatures [see, for example, Encyclopedia of Polymer Science and Engineering, Vol. 11, page 664 (1988)]. Examples of typical polycarbonate and polyester carbonate heat stabilizers are phosphorus compounds, for example aromatic phosphines, phosphites and phosphonates.

It is also known that siloxane compounds cart be used to stabilize polycarbonates against the effects of high temperatures (see German patent application P 4 118 705.9 (Le A 28 445) and U.S. Pat. No. 4,197,384).

However, the effect of the Si compounds according to the invention on the stability of thermoplastic polycarbonates against the effects of high temperatures is neither known nor logical. Surprisingly, they protect polycarbonates particularly effectively against yellowing under the effect of heat and, in particular, lead to surprisingly high light transmission values of the polycarbonates, even after prolonged thermal ageing.

The addition of siloxanes to polycarbonates for stabilization is also known from DE-OS 2 920 450 (Le A 19 566), DE-OS 2 920 451 (Le A 19 567), DE-OS 3 026 503 (Le A 20 430) and DE-OS 3 222 522 (Le A 21 688).

Whereas the siloxane compounds according to DE-OS 3 026 503 (Le A 20 430) and DE-OS 3 222 522 (Le A 21 688) only develop their stabilizing effect in combination with other phosphorus-containing additives, the silicon-containing compounds according to the invention have a stabilizing effect even in the absence of other additives. According to DE-OS 2 920 451, oxetanes, dioxanes or tetrahydrofurans are additionally present.

The siloxanes according to DE-OS 2 920 450 (Le A 19 566) also have a stabilizing effect on polycarbonates in the absence of other additives, but do not provide for such high fight transmission values, particularly after thermal ageing, as the silicon/alkylene glycol derivatives according to the invention.

Polycarbonates to be stabilized in accordance with the invention are thermoplastic aromatic homopolycarbonates and copolycarbonates based, for example, on one or more of the following diphenols: hydroquinone, resorcinol, dihydroxydiphenyls, bis-(hydroxyphenyl)-alkanes, bis-(hydroxyphenyl)-cycloalkanes, bis-(hydroxyphenyl)-sulfides, bis-(hydroxyphenyl)-ethers, bis-(hydroxyphenyl)ketones, bis-(hydroxyphenyl)-sulfoxides, bis-(hydroxyphenyl)-sulfones, $\alpha,\alpha'$-bis-(hydroxyphenyl)-diisopropyl benzenes and nucleus-alkylated and nucleus-halogenated compounds thereof. These and other suitable diphenols are described, for example, in U.S. Pat. Nos. 3,028,365, 3,275,601, 3,148,172, 3,062,781, 2,991,273, 3,271,367, 2,999,835, 4,982,014 and 2,999,846; in DE-OSS 1 570 703, 2 063 050, 2 063 052, 2 211 956, 2 211 957, in FR-PS 1 561 518 and in the book by H. Schnell entitled "Chemistry and Physics of Polycarbonates", Interscience Publishers, New York, 1964.

Preferred diphenols are, for example, 4,4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-cyclohexane, $\alpha,\alpha'$-bis-(4-hydroxyphenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethylhydroxyphenyl)methane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, 1,1-bis-(4-hydroxyphenyl)-3,3,5-trimethylcyclohexane, $\alpha,\alpha'$-bis-(3,5-dimethyl-4-hydroxyphenyl)-p-diisopropylbenzene and 2,2-bis-(3,5-dichloro-4-hydroxyphenyl)-propane.

Particularly preferred diphenols are, for example, 2,2-bis-(4-hydroxyphenyl)propane, 2,2-bis-(3,5-dimethylhydroxyphenyl)-propane, 2,2-bis-(3,5-dichloro-4-hydroxyphenyl)-propane, 2,2-bis-(3,5-dibromo-4-hydroxyphenyl)-propane, 1,1-bis-(4-hydroxyphenyl)-cyclohexane and 1,1-bis-(4-hydroxyphenyl)-3,3,5-trimethylcyclohexane.

Preferred aromatic polycarbonates are those based on one or more of the diphenols mentioned as preferred. Particularly preferred aromatic polycarbonates are copolycarbonates based on 2,2-bis-(hydroxyphenyl)-propane and one of the other diphenols mentioned as particularly preferred. Polycarbonates based solely on 2,2-bis-(4-hydroxyphenyl)-propane are also particularly preferred.

The aromatic polycarbonates may be produced by known methods, for example by the melt transesterification process from bisphenol and diphenyl carbonate and the two-phase interfacial process from bisphenols and phosgene which is described in the literature cited above. The aromatic polycarbonates can also be branched by incorporation of three - or more than three - functional compounds.

Aromatic polycarbonates of this type are described, for example, in DE-OSS 1 570 533, 1 595 762, 2 116 974, 2 113 347, in GB-PS 1,079,821, in U.S. Pat. No. 3,544,514 and in DE-OS 2 500 092.

Some of the compounds containing three or more than three phenolic hydroxy groups which may be used in accordance with the invention are, for example, phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri(4-hydroxyphenyl)-ethane, tri-(4-hydroxyphenyl)-phenyl methane, 2,2-bis-[4,4-bis-(4-hydroxyphenyl)-cyclohexyl]-propane, 2,4-bis-(4-hydroxyphenylisopropyl)-phenol, 2,6-bis-(2'-hydroxy-5'-methylbenzyl)4-methylphenol, 2-(4-hydroxyphenyl)-2-(2,4-dihydroxyphenyl)-propane, hexa-[4-(4-hydroxyphenylisopropyl)-phenyl]-orthoterephthalic acid ester, tetra-(4-hydroxyphenylisopropyl)-phenoxy)-methane and 1,4-bis-[(4',4''-dihydroxytriphenyl)-methyl]-benzene. Some of the other trifunctional compounds are 2,4-dihydroxybenzoic acid, trimesic acid, cyanuric chloride and 3,3-bis-(4-hydroxy-3-methylphenyl)-2-oxo-2,3-dihydroindole.

The aromatic polycarbonates should generally have weight average molecular weights Mw in the range from 10,000 to more than 200,000 and preferably in the range from 20,000 to 80,000, as determined by measurement of the relative viscosity in $CH_2Cl_2$ at 25° C. and at a concentration of 0.5 g/dl.

The molecular weight Mw of the polycarbontes is established in known manner by the use of chain terminators, such as for example phenol or halophenols or alkylphenols, in the calculated quantities.

Polyester carbonates to be stabilized in accordance with the invention are aromatic polyester carbonates synthesized from at least one aromatic bisphenol, at least one aromatic dicarboxylic acid and carbonic acid.

Suitable aromatic dicarboxylic acids are, for example, orthophthalic acid, terephthalic acid, isophthalic acid, tert. butyl isophthalic acid, 3,3'-diphenyl dicarboxylic acid, 4,4'-diphenyl dicarboxylic acid, 4,4'-diphenyl ether dicarboxylic acid, 4,4'-benzophenone dicarboxylic acid, 3,4'-benzophenone dicarboxylic acid, 4,4'-diphenyl sulfone dicarboxylic acid, 2,2-bis-(4-caxboxyphenyl)-propane, trimethyl-3-phenylindane-4,5'-dicarboxylic acid.

Of the aromatic dicarboxylic acids, terephthalic acid and/or isophthalic acid axe particularly preferred.

The aromatic polyester carbonates may be produced by processes known from the literature for the production of polycarbonates, for example by the process in homogeneous solution, by the melt transesterification process and by the two-phase interfacial process.

Melt transesterification processes are described, for example in U.S. Pat. No. 3,494,885, 4,386,186, 4,661,580, 4,680, 371 and 4,680,372, in EP-A 26 120, 26 121, 84, 28 030, 39 845, 91 602, 97 780, 79 075, 146 887, 156 103, 234 913, 234 and 240 301 and in DE-ASS 1 495 626 and 2 232 877. The two-phase interfacial process is described, for example, in EP-A 68 014, 88 322, 134 898, 151 750, 182 189, 219 708, 272 426; in DE-OSS 2 940 024, 3 007 934, 3 440 020 and in Polymer Reviews, Vol. 10, "Condensation Polymers by Interfacial and Solution Methods", Paul W. Morgan, Interscience Publishers, New York 1965, Chapter III, page 325, Polyesters.

Suitable silicon compounds are preferably those corresponding to formulae (II) and/or (III)

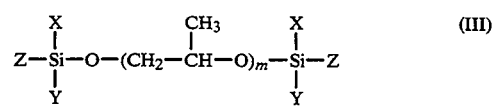

in which

X is an alkyl, aryl, alkoxy, alkoxyoxetane or alkoxyether group containing 1 to 20 carbon atoms, Y is an alkyl, aryl, alkoxy, alkoxyoxetane or alkoxyether group containing 1 to 20 carbon atoms, Z is a methyl or a phenyl group and m is an integer of 1 to 100, preferably 1 to 50 and, more preferably, 1 to 20.

Suitable examples of (II) are those corresponding to formulae (IIa), (IIb) and (IIc)

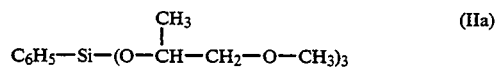

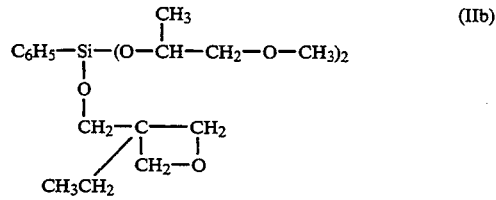

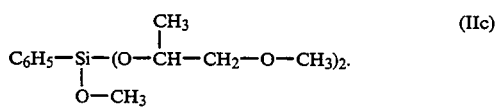

Suitable examples of (III) are those corresponding to formula (IIIa):

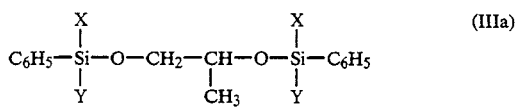

in which
X=Y-O-CH(CH₃)CH₂OCH₃ or

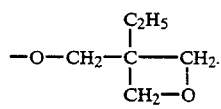

Suitable examples of (I) are those corresponding to formula (Ia)

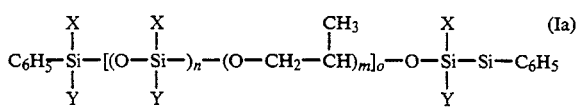

in which
n=1, m=1 and o=8,
X=Y -OCH(CH₃)CH₂-OCH₃ or

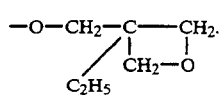

The silicon compounds are incorporated in the thermoplastic polycarbonates and polyester carbonates in known manner preferably during the production of moldings or films.

Accordingly, the present invention also relates to a process for the production of the mixtures according to the invention, characterized in that compounds corresponding to formula (I) and/or (II) and/or (III) are incorporated in thermoplastic polycarbonates and/or polyester carbonates in quantities of 0.01% by weight to 20.0% by weight and preferably in quantities of 0.01% by weight to 10% by weight and especially of 0.05% by weight to 5.0% by weight, based on the quantity of polycarbonate and/or polyester carbonate used, via the polycarbonate or polyester carbonate melt or via a solution of the polycarbonates or polyester carbonates in known inert solvents and the mixtures obtained are cooled and granulated, optionally after evaporation of the solvent, and are preferably directly processed to moldings or cast to films.

Typical additives, such as mold release agents, plasticizers, fillers and reinforcing materials, may be added in known manner to the polycarbonates and/or polyester carbonates to be stabilized in known manner.

The polycarbonates and/or polyester carbonates stabilized in accordance with the invention may be processed to moldings of various kinds in known manner by extrusion or injection molding.

The polycarbonates stabilized in accordance with the invention are processed, for example, in extruders or kneaders or from solutions to form moldings of various kinds, for example to spectacles, baby bottles, water containers and films.

The treatment of the stabilized polycarbonate and/or polyester carbonate moldings at high temperatures is carried out, for example, by hot air ageing for 1000 hours at 130° C. Transmission was determined in accordance with ASTM 1003 while the yellowness index was determined in accordance with ASTM D.

Suitable moldings of the polycarbonates and/or polyester carbonates stabilized in accordance with the invention are, for example, panels, more particularly double-walled panels, compact discs, electrical insulating films. Accordingly, the polycarbonates and/or polyester carbonates stabilized in accordance with the invention are industrially used, for example, in the building industry, in the fighting field, in the optical field and in the electrical industry.

EXAMPLES

Components used for stabilization:
1. Triphenyl phosphine
2. A phosphite corresponding to the following formula

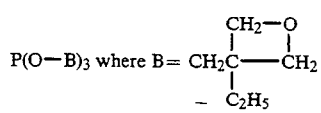

3. A silicon/propylene glycol derivative corresponding to the formula

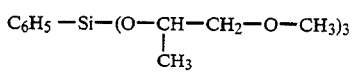

4. A silicon/propylene glycol derivative corresponding to the formula

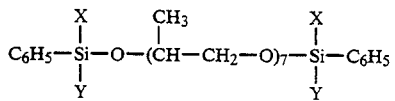

in which
X=Y=OCH(CH₃)CH₂OCH₃

All the components were used in phenol-terminated bisphenol A polycarbonate, Mw 28,000.

A) Synthesis of the stabilizers
Component 3
Tri-( 1 -methoxypropyl-2-oxy)-phenyl silane
190.2 g (2.11 mol) 1-methoxy-2-propanol and 223.7 g (2.21 mol) triethyl amine are initially introduced under nitrogen at room temperature in 1000 g toluene (solution I). 148.1 g (0.70 too! ) trichlorophenyl silane dissolved in 300 g toluene are then added dropwise under nitrogen over a period of 30 minutes at room temperature (solution II), after which the solution is heated to 60° to 70° C.

After stirring for 4 hours at that temperature, the mixture is worked up as follows:
The salt is filtered off and washed with 500 ntl toluene, the tiltrate is acidified with 10% hydrochloric acid and washed free from electrolyte with distilled water, the toluene is removed in a water jet pump vacuum at max. 70° C and the residue is distilled in an oil pump vacuum at a maximum sump temperature of 150° C.
Yield: 164 g
Component 4

A typical preparation of the silicon/propylene glycol compounds corresponding to formula III is as follows:

162.21 g 1-methoxy-2-propanol were dissolved and stirred in 1500 ml toluene. 196.71 g triethyl amine were added. After purging with nitrogen, 126.93 g phenyl trichlorosilane were slowly added dropwise. The solution was stirred for 4 hours. The product was washed with water and dried.

B) Production of the mixtures

The additives were incorporated by co-extrusion in a polycarbonate resin (bisphenol A homopolycarbonate, $nre_I$ 1.28, as measured in $CH_2Cl_2$ at 25° C. and at a concentration of 0.5 g in 100 ml $CH_2Cl_2$), followed by injection molding. The injection moldings were aged in hot air at 130° C. The yellowness indices (YI) and % transmissions were measured after 0, 500 and 1000 hours. Table 1 shows the results measured on 4 mm thick plates for the polycarbonates and the additive-containing compositions. Table 2 shows the % transmissions for the same compositions.

TABLE 1

| Composition | YI (0 h) | YI (500 h) | YI (1000 h) |
| --- | --- | --- | --- |
| Additive-free polycarbonate | 4.2 | 7.8 | 11.2* |
| 0.1% Component 1 | 2.8 | 6.7 | 11.1* |
| 0.4% Component 1 | 2.6 | 6.6 | 11.0* |
| 0.1% Component 2 | 4.1 | 7.1 | 10.9* |
| 0.4% Component 3 | 3.0 | 5.8 | 7.9** |
| 0.4% Component 4 | 3.3 | 6.3 | 9.2** |

*Comparison
**Invention

TABLE 2

| Composition | % Transmission (0 h) | % Transmission (500 h) | % Transmission (1000 h) |
| --- | --- | --- | --- |
| Additive-free polycarbonate | 89.35 | 88.52 | 87.57* |
| 0.1% Component 1 | 89.30 | 88.35 | 87.30* |
| 0.4% Component 1 | 89.35 | 88.42 | 87.35* |
| 0.1% Component 2 | 88.83 | 88.25 | 87.27* |
| 0.4% Component 3 | 89.92 | 89.60 | 89.02** |
| 0.4% Component 4 | 90.34 | 89.66 | 88.89** |

*Comparison
**Invention

We claim:
1. A thermoplastic molding composition comprising
 (a) a resin selected from the group consisting of polycarbonate and polyester carbonate, and
 (b) about 0.01 to 20.0 percent of at least one silicon compound selected from the group consisting of

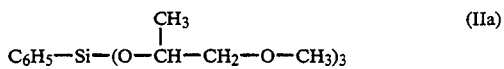

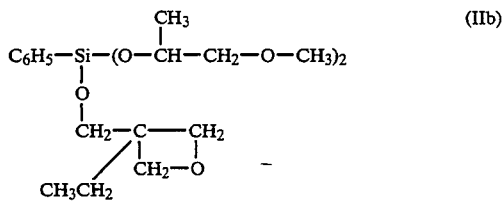

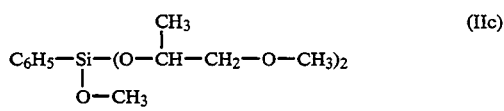

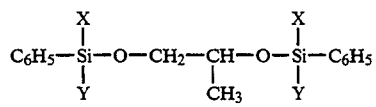

in which
X and Y, both denote -OCH(CH3)CH2)-OCH3 or

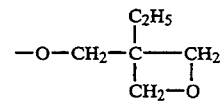

and

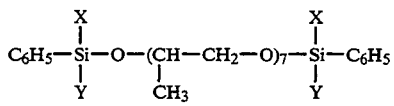

in which X and Y both denote OCH(CH3)CH2OCH3.

* * * * *